(12) United States Patent
Lea et al.

(10) Patent No.: US 8,318,440 B2
(45) Date of Patent: Nov. 27, 2012

(54) SYNTHETIC PEPTIDES IMMUNO-REACTIVE WITH RHEUMATOID ARTHRITIS AUTO-ANTIBODIES

(75) Inventors: Peter Lea, Toronto (CA); Mingfu Ling, Toronto (CA)

(73) Assignee: SQI Diagnostics Systems Inc., Toronto, Ontario (CA)

( * ) Notice: Subject to any disclaimer, the term of this patent is extended or adjusted under 35 U.S.C. 154(b) by 216 days.

(21) Appl. No.: 12/734,894

(22) PCT Filed: Dec. 3, 2008

(86) PCT No.: PCT/CA2008/002109
§ 371 (c)(1),
(2), (4) Date: Oct. 22, 2010

(87) PCT Pub. No.: WO2009/070875
PCT Pub. Date: Jun. 11, 2009

(65) Prior Publication Data
US 2011/0065134 A1    Mar. 17, 2011

(30) Foreign Application Priority Data

Dec. 3, 2007  (CA) ........................................ 2613075
Oct. 21, 2008 (CA) ........................................ 2641448

(51) Int. Cl.
*G01N 33/53*    (2006.01)

(52) U.S. Cl. .......................................... 435/7.1; 436/518
(58) Field of Classification Search ................... None
See application file for complete search history.

(56) References Cited

FOREIGN PATENT DOCUMENTS

| WO | WO 98/22503 A2 | 5/1998 |
| WO | WO 99/28344 A2 | 6/1999 |
| WO | WO 01/46222 A2 | 6/2001 |
| WO | WO 03/050542 A2 | 6/2003 |
| WO | WO 2004/087747 A2 | 10/2004 |
| WO | WO 2009/070875 A2 | 6/2009 |

OTHER PUBLICATIONS

Schellekens et al., Citrulline is an essential constituent of antigenic determinants recognized by rheumatoid arthritis-specific autoantibodies, J. Clin. Invest., Jan. 1998, vol. 101, No. 1, pp. 273-281.
PCT International Search Report, PCT/CA2008/002109, dated Jan. 19, 2009.
PCT International Preliminary Report on Patentability, PCT/CA2008/002109 dated Jun. 8, 2010.

*Primary Examiner* — Jacob Cheu
(74) *Attorney, Agent, or Firm* — TraskBritt

(57) ABSTRACT

Embodiments of the present invention relate to a three dimensional matrix of selected, synthetic peptide mimic sequences that are preferentially recognized by auto-antibodies, specifically by autoimmune antibodies, to be detected in patients afflicted with rheumatic arthritis, enabling enhanced sensitivity and specificity in detection of these antibodies in pre-symptomatic patients, in patients showing symptoms as well as patients confirmed positive for rheumatoid arthritis.

20 Claims, 5 Drawing Sheets $$
\begin{array}{lll}
\overset{1}{\text{CKSHQESTXGXSRSRGRSGC}} = \text{X G X} & \text{[SEQ ID NO:17]} \\[4pt]
\overset{\phantom{xx}2}{\text{CKRDGSXHPXRSHDC}} = \text{X HP X} & \text{[SEQ ID NO:24]} \\[4pt]
\overset{\phantom{xxxx}2}{\text{CKSHQESVXLGXSRSRGS}} = \text{X LG X} & \text{[SEQ ID NO:27]} \\[4pt]
\overset{\phantom{xxxx}3}{\text{CKDNSDXSTYXWTRCK}} = \text{X STY X} & \text{[SEQ ID NO:30]} \\[4pt]
\overset{\phantom{xxxx}0}{\text{CSHQESTXXSRSRGRSGCK}} = \text{XX} & \text{[SEQ ID NO:19]} \\[4pt]
\overset{\phantom{xxxxx}5}{\text{CSHQESTXGGGGSXSRSRCK}} = \text{X GGGGS X} & \text{[SEQ ID NO:20]} \\[4pt]
\overset{\phantom{xxxxxx}6}{\text{CSHQESTXGGGGSGXSRSRCK}} = \text{X GGGGSG X} & \text{[SEQ ID NO:21]} \\[4pt]
\overset{\phantom{xxx}1\phantom{xx}1}{\text{CSHQESTXGXG XSRSRCK}} = \text{X G X G X} & \text{[SEQ ID NO:22]} \\[4pt]
\overset{\phantom{xxxx}2}{\text{CKSHQESVXLGXSRSRGSC}} = \text{X LG X} & \text{[SEQ ID NO:28]}
\end{array}
$$

| Sequence # | Code | Original peptides | | | | | | | | | | | | | | | | | |
|---|---|---|---|---|---|---|---|---|---|---|---|---|---|---|---|---|---|---|---|
| 1 | CCP-1 | C | K | S | G | G | S | T | CIT | C | G | CIT | S | S | R | D | G | C | |
| 2 | CCP-2 | C | K | S | G | G | S | T | CIT | G | R | R | D | G | C | | | | |
| 3 | CCP-3 | C | K | S | G | G | S | T | CIT | S | S | R | D | G | C | | | | |
| 4 | CCP-4 | C | S | H | Q | E | S | T | CIT | G | R | S | R | G | R | S | C | | |
| 5 | CCP-5 | C | S | H | Q | E | S | T | CIT | S | R | S | R | G | R | S | C | | |
| 6 | CCP-6 | C | S | H | Q | E | S | T | CIT | G | G | CIT | S | R | S | R | G | R | S | C |
| 7 | CCP-7 | K | S | G | G | G | S | CIT | G | G | CIT | S | R | R | D | G | | | |
| 8 | CCP-8 | C | R | D | G | S | CIT | H | P | CIT | R | S | H | D | C | | | | |
| 9 | CCP-9 | C | S | S | T | G | C | CIT | Q | G | CIT | S | H | H | E | C | | | |
| 10 | CCP-10 | C | S | H | Q | E | S | V | CIT | L | G | CIT | S | R | S | R | G | S | |
| 11 | CCP-11 | C | D | N | Y | W | S | F | S | D | CIT | S | T | Y | CIT | W | T | R | C |
| | CP-1 derivatives | | | | | | | | | | | | | | | | | | |
| 12 | CCP-1 | C | K | S | G | G | S | T | CIT | C | G | CIT | S | S | R | D | G | C | |
| 13 | CCP-1B | C | K | S | G | G | S | T | CIT | G | CIT | S | R | R | D | G | G | C | |
| 14 | CCP-1C | C | K | S | G | G | S | T | CIT | G | G | S | CIT | S | R | R | D | G | C |
| | CCP-6 derivatives | | | | | | | | | | | | | | | | | | |
| 15 | CCP-6 | C | S | H | Q | E | S | T | CIT | G | G | CIT | S | R | S | R | G | R | S | C |
| 16 | CCP-6B | C | S | H | Q | E | S | T | CIT | G | CIT | S | R | S | R | G | R | S | G | C |
| 17 | CCP-6B2 | C | K | S | H | Q | E | S | T | CIT | G | CIT | S | R | S | R | G | R | S | G | C |
| 18 | CCP-6C | C | S | H | Q | E | S | T | CIT | G | G | G | S | CIT | S | R | S | R | G | R | S | C |
| 19 | CCP-6D | C | S | H | Q | E | S | T | CIT | CIT | S | R | S | R | G | R | S | G | C | K |
| 20 | CCP-6E | C | S | H | Q | E | S | T | CIT | G | G | G | S | CIT | S | R | S | R | C | K |
| 21 | CCP-6F | C | S | H | Q | E | S | T | CIT | G | G | G | S | G | CIT | S | R | S | R | C | K |
| 22 | CCP-6G | C | S | H | Q | E | S | T | CIT | G | CIT | G | CIT | S | R | S | R | C | K |
| | CCP-8 derivatives | | | | | | | | | | | | | | | | | | |
| 23 | CCP-8 | C | R | D | G | S | CIT | H | P | CIT | R | S | H | D | C | | | | |
| 24 | CCP-8B | C | K | R | D | G | S | CIT | H | P | CIT | R | S | H | D | C | | | |
| 25 | CCP-8C | C | R | D | G | S | CIT | H | P | CIT | R | S | H | D | C | K | | | |
| | CCP-10 derivatives | | | | | | | | | | | | | | | | | | |
| 26 | CCP-10 | C | S | H | Q | E | S | V | CIT | L | G | CIT | S | R | S | R | G | S | |
| 27 | CCP-10B | C | K | S | H | Q | E | S | V | CIT | L | G | CIT | S | R | S | R | G | S |
| 28 | CCP-10C | C | K | S | H | Q | E | S | V | CIT | L | G | CIT | S | R | S | R | G | S | C |
| | CCP-11 derivatives | | | | | | | | | | | | | | | | | | |
| 29 | CCP-11 | C | D | N | Y | W | S | F | S | D | CIT | S | T | Y | CIT | W | T | R | C |
| 30 | CCP-11B | C | K | D | N | S | D | CIT | S | T | Y | CIT | W | T | R | C | K | | |
| 31 | CCP-11C | C | K | D | N | S | D | CIT | S | T | Y | CIT | W | T | R | C | K | K | |
| 32 | CCP-11D | C | K | D | N | S | D | CIT | S | T | Y | CIT | T | R | C | K | K | | |
| 33 | CCP-11E | K | C | K | D | N | S | D | CIT | S | T | Y | CIT | W | T | R | C | K | K |

SEQUENCE LISTING

```
<160> NUMBER OF SEQ ID NOS: 33

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(18)
<223> OTHER INFORMATION: Xaa is citrulline

<400> SEQUENCE: 1

Cys Lys Ser Gly Gly Gly Ser Thr Xaa Cys Gly Xaa Ser Ser Arg Asp
1               5                   10                  15

Gly Cys
```

```
<210> SEQ ID NO 2
<211> LENGTH: 15
<212> TYPE: PRT
<213> ORGANISM: Artificial Sequence
<220> FEATURE:
<223> OTHER INFORMATION: SYNTHETIC PEPTIDE
<220> FEATURE:
<221> NAME/KEY: Xaa
<222> LOCATION: (1)..(15)
<223> OTHER INFORMATION: Xaa is citrulline

<400> SEQUENCE: 2

Cys Lys Ser Gly Gly Gly Ser Thr Xaa Gly Arg Arg Asp Gly Cys
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthetic Peptide
<220> FEATURE:
<221> NAME/KEY: Xaa
<222> LOCATION: (1)..(15)
<223> OTHER INFORMATION: Xaa is citrulline

<400> SEQUENCE: 3

Cys Lys Ser Gly Gly Gly Ser Thr Xaa Ser Ser Arg Asp Gly Cys
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(16)
<223> OTHER INFORMATION: Xaa is citrulline

<400> SEQUENCE: 4

Cys Ser His Gln Glu Ser Thr Xaa Gly Arg Ser Arg Gly Arg Ser Cys
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(16)
<223> OTHER INFORMATION: Xaa is citrulline

<400> SEQUENCE: 5

Cys Ser His Gln Glu Ser Thr Xaa Ser Arg Ser Arg Gly Arg Ser Cys
1               5                   10                  15

<210> SEQ ID NO 6
<211> LENGTH: 19
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(19)
<223> OTHER INFORMATION: Xaa is citrulline
```

```
<400> SEQUENCE: 6

Cys Ser His Gln Glu Ser Thr Xaa Gly Gly Xaa Ser Arg Ser Arg Gly
1               5                   10                  15

Arg Ser Cys

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(15)
<223> OTHER INFORMATION: Xaa is citrulline

<400> SEQUENCE: 7

Lys Ser Gly Gly Gly Ser Xaa Gly Gly Xaa Ser Arg Arg Asp Gly
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(14)
<223> OTHER INFORMATION: Xaa is citrulline

<400> SEQUENCE: 8

Cys Arg Asp Gly Ser Xaa His Pro Xaa Arg Ser His Asp Cys
1               5                   10

<210> SEQ ID NO 9
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(15)
<223> OTHER INFORMATION: Xaa is citrulline

<400> SEQUENCE: 9

Cys Ser Ser Thr Gly Cys Xaa Gln Gly Xaa Ser His His Glu Cys
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(17)
<223> OTHER INFORMATION: Xaa is citrulline

<400> SEQUENCE: 10

Cys Ser His Gln Glu Ser Val Xaa Leu Gly Xaa Ser Arg Ser Arg Gly
1               5                   10                  15

Ser
```

```
<210> SEQ ID NO 11
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: Xaa
<222> LOCATION: (1)..(18)
<223> OTHER INFORMATION: Xaa is citrulline

<400> SEQUENCE: 11

Cys Asp Asn Tyr Trp Ser Phe Ser Asp Xaa Ser Thr Tyr Xaa Trp Thr
1               5                   10                  15

Arg Cys

<210> SEQ ID NO 12
<211> LENGTH: 18
<212> TYPE: PRT
<213> ORGANISM: Artificial Sequence
<220> FEATURE:
<223> OTHER INFORMATION: Synthetic peptide derived from SEQ ID NO 1
<220> FEATURE:
<221> NAME/KEY: Xaa
<222> LOCATION: (1)..(18)
<223> OTHER INFORMATION: Xaa is citrulline

<400> SEQUENCE: 12

Cys Lys Ser Gly Gly Gly Ser Thr Xaa Cys Gly Xaa Ser Ser Arg Asp
1               5                   10                  15

Gly Cys

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide derived from SEQ ID NO 1
<220> FEATURE:
<221> NAME/KEY: Xaa
<222> LOCATION: (1)..(18)
<223> OTHER INFORMATION: Xaa is citrulline

<400> SEQUENCE: 13

Cys Lys Ser Gly Gly Gly Ser Thr Xaa Gly Xaa Ser Arg Arg Asp Gly
1               5                   10                  15

Gly Cys

<210> SEQ ID NO 14
<211> LENGTH: 20
<212> TYPE: PRT
<213> ORGANISM: Artificial Sequence
<220> FEATURE:
<223> OTHER INFORMATION: Synthetic peptide derived from SEQ ID NO 1
<220> FEATURE:
<221> NAME/KEY: Xaa
<222> LOCATION: (1)..(20)
<223> OTHER INFORMATION: Xaa is citrulline

<400> SEQUENCE: 14

Cys Lys Ser Gly Gly Gly Ser Thr Xaa Gly Gly Gly Ser Xaa Ser Arg
1               5                   10                  15

Arg Asp Gly Cys
            20
```

```
<210> SEQ ID NO 15
<211> LENGTH: 19
<212> TYPE: PRT
<213> ORGANISM: Artificial Sequence
<220> FEATURE:
<223> OTHER INFORMATION: Synthetic peptide derived from SEQ ID NO 6
<220> FEATURE:
<221> NAME/KEY: Xaa
<222> LOCATION: (1)..(19)
<223> OTHER INFORMATION: Xaa is citrulline

<400> SEQUENCE: 15

Cys Ser His Gln Glu Ser Thr Xaa Gly Gly Xaa Ser Arg Ser Arg Gly
1               5                   10                  15

Arg Ser Cys

<210> SEQ ID NO 16
<211> LENGTH: 19
<212> TYPE: PRT
<213> ORGANISM: Artificial Sequence
<220> FEATURE:
<223> OTHER INFORMATION: Synthetic peptide derived from SEQ ID NO 6
<220> FEATURE:
<221> NAME/KEY: Xaa
<222> LOCATION: (1)..(19)
<223> OTHER INFORMATION: Xaa is citrulline

<400> SEQUENCE: 16

Cys Ser His Gln Glu Ser Thr Xaa Gly Xaa Ser Arg Ser Arg Gly Arg
1               5                   10                  15

Ser Gly Cys

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide derived from SEQ ID NO 6
<220> FEATURE:
<221> NAME/KEY: Xaa
<222> LOCATION: (1)..(20)
<223> OTHER INFORMATION: Xaa is citrulline

<400> SEQUENCE: 17

Cys Lys Ser His Gln Glu Ser Thr Xaa Gly Xaa Ser Arg Ser Arg Gly
1               5                   10                  15

Arg Ser Gly Cys
            20

<210> SEQ ID NO 18
<211> LENGTH: 21
<212> TYPE: PRT
<213> ORGANISM: Artificial Sequence
<220> FEATURE:
<223> OTHER INFORMATION: Synthetic peptide derived from SEQ ID NO 6
<220> FEATURE:
<221> NAME/KEY: Xaa
<222> LOCATION: (1)..(21)
<223> OTHER INFORMATION: Xaa is citrulline

<400> SEQUENCE: 18

Cys Ser His Gln Glu Ser Thr Xaa Gly Gly Gly Ser Xaa Ser Arg Ser
1               5                   10                  15

Arg Gly Arg Ser Cys
            20
```

```
<210> SEQ ID NO 19
<211> LENGTH: 19
<212> TYPE: PRT
<213> ORGANISM: Artificial Sequence
<220> FEATURE:
<223> OTHER INFORMATION: Synthetic peptide derived from SEQ ID NO 6
<220> FEATURE:
<221> NAME/KEY: Xaa
<222> LOCATION: (1)..(19)
<223> OTHER INFORMATION: Xaa is citrulline

<400> SEQUENCE: 19

Cys Ser His Gln Glu Ser Thr Xaa Xaa Ser Arg Ser Arg Gly Arg Ser
1               5                   10                  15

Gly Cys Lys

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide derived from SEQ ID NO 6
<220> FEATURE:
<221> NAME/KEY: Xaa
<222> LOCATION: (1)..(20)
<223> OTHER INFORMATION: Xaa is citrulline

<400> SEQUENCE: 20

Cys Ser His Gln Glu Ser Thr Xaa Gly Gly Gly Gly Ser Xaa Ser Arg
1               5                   10                  15

Ser Arg Cys Lys
            20

<210> SEQ ID NO 21
<211> LENGTH: 21
<212> TYPE: PRT
<213> ORGANISM: Artificial Sequence
<220> FEATURE:
<223> OTHER INFORMATION: Synthetic peptide derived from SEQ ID NO 6
<220> FEATURE:
<221> NAME/KEY: Xaa
<222> LOCATION: (1)..(21)
<223> OTHER INFORMATION: Xaa is citrulline

<400> SEQUENCE: 21

Cys Ser His Gln Glu Ser Thr Xaa Gly Gly Gly Gly Ser Gly Xaa Ser
1               5                   10                  15

Arg Ser Arg Cys Lys
            20

<210> SEQ ID NO 22
<211> LENGTH: 18
<212> TYPE: PRT
<213> ORGANISM: Artificial Sequence
<220> FEATURE:
<223> OTHER INFORMATION: Synthetic peptide derived from SEQ ID NO 6
<220> FEATURE:
<221> NAME/KEY: Xaa
<222> LOCATION: (1)..(18)
<223> OTHER INFORMATION: Xaa is citrulline

<400> SEQUENCE: 22

Cys Ser His Gln Glu Ser Thr Xaa Gly Xaa Gly Xaa Ser Arg Ser Arg
1               5                   10                  15

Cys Lys
```

```
<210> SEQ ID NO 23
<211> LENGTH: 14
<212> TYPE: PRT
<213> ORGANISM: Artificial Sequence
<220> FEATURE:
<223> OTHER INFORMATION: Synthetic peptide derived from SEQ ID NO 8
<220> FEATURE:
<221> NAME/KEY: Xaa
<222> LOCATION: (1)..(14)
<223> OTHER INFORMATION: Xaa is citrulline

<400> SEQUENCE: 23

Cys Arg Asp Gly Ser Xaa His Pro Xaa Arg Ser His Asp Cys
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic peptide derived from SEQ ID NO 8
<220> FEATURE:
<221> NAME/KEY: Xaa
<222> LOCATION: (1)..(15)
<223> OTHER INFORMATION: Xaa is citrulline

<400> SEQUENCE: 24

Cys Lys Arg Asp Gly Ser Xaa His Pro Xaa Arg Ser His Asp Cys
1               5                   10                  15

<210> SEQ ID NO 25
<211> LENGTH: 15
<212> TYPE: PRT
<213> ORGANISM: Artificial Sequence
<220> FEATURE:
<223> OTHER INFORMATION: Synthetic peptide derived from SEQ ID NO 8
<220> FEATURE:
<221> NAME/KEY: Xaa
<222> LOCATION: (1)..(15)
<223> OTHER INFORMATION: Xaa is citrulline

<400> SEQUENCE: 25

Cys Arg Asp Gly Ser Xaa His Pro Xaa Arg Ser His Asp Cys Lys
1               5                   10                  15

<210> SEQ ID NO 26
<211> LENGTH: 17
<212> TYPE: PRT
<213> ORGANISM: Artificial Sequence
<220> FEATURE:
<223> OTHER INFORMATION: Synthetic peptide derived from SEQ ID NO 10
<220> FEATURE:
<221> NAME/KEY: Xaa
<222> LOCATION: (1)..(17)
<223> OTHER INFORMATION: Xaa is citrulline

<400> SEQUENCE: 26

Cys Ser His Gln Glu Ser Val Xaa Leu Gly Xaa Ser Arg Ser Arg Gly
1               5                   10                  15

Ser

<210> SEQ ID NO 27
<211> LENGTH: 18
<212> TYPE: PRT
<213> ORGANISM: Artificial Sequence
<220> FEATURE:
<223> OTHER INFORMATION: Synthetic peptide derived from SEQ ID NO 10
<220> FEATURE:
<221> NAME/KEY: Xaa
<222> LOCATION: (1)..(18)
<223> OTHER INFORMATION: Xaa is citrulline
```

-continued

```
<400> SEQUENCE: 27

Cys Lys Ser His Gln Glu Ser Val Xaa Leu Gly Xaa Ser Arg Ser Arg
1               5                   10                  15

Gly Ser

<210> SEQ ID NO 28
<211> LENGTH: 19
<212> TYPE: PRT
<213> ORGANISM: Artificial Sequence
<220> FEATURE:
<223> OTHER INFORMATION: Synthetic peptide derived from SEQ ID NO 10
<220> FEATURE:
<221> NAME/KEY: Xaa
<222> LOCATION: (1)..(19)
<223> OTHER INFORMATION: Xaa is citrulline

<400> SEQUENCE: 28

Cys Lys Ser His Gln Glu Ser Val Xaa Leu Gly Xaa Ser Arg Ser Arg
1               5                   10                  15

Gly Ser Cys

<210> SEQ ID NO 29
<211> LENGTH: 18
<212> TYPE: PRT
<213> ORGANISM: Artificial Sequence
<220> FEATURE:
<223> OTHER INFORMATION: Synthetic peptide derived from SEQ ID NO 11
<220> FEATURE:
<221> NAME/KEY: Xaa
<222> LOCATION: (1)..(18)
<223> OTHER INFORMATION: Xaa is citrulline

<400> SEQUENCE: 29

Cys Asp Asn Tyr Trp Ser Phe Ser Asp Xaa Ser Thr Tyr Xaa Trp Thr
1               5                   10                  15

Arg Cys

<210> SEQ ID NO 30
<211> LENGTH: 16
<212> TYPE: PRT
<213> ORGANISM: Artificial Sequence
<220> FEATURE:
<223> OTHER INFORMATION: Synthetic peptide derived from SEQ ID NO 11
<220> FEATURE:
<221> NAME/KEY: Xaa
<222> LOCATION: (1)..(16)
<223> OTHER INFORMATION: Xaa is citrulline

<400> SEQUENCE: 30

Cys Lys Asp Asn Ser Asp Xaa Ser Thr Tyr Xaa Trp Thr Arg Cys Lys
1               5                   10                  15

<210> SEQ ID NO 31
<211> LENGTH: 18
<212> TYPE: PRT
<213> ORGANISM: Artificial Sequence
<220> FEATURE:
<223> OTHER INFORMATION: Synthetic peptide derived from SEQ ID NO 11
<220> FEATURE:
<221> NAME/KEY: Xaa
<222> LOCATION: (1)..(18)
<223> OTHER INFORMATION: Xaa is citrulline

<400> SEQUENCE: 31

Cys Lys Asp Asn Ser Asp Xaa Ser Thr Tyr Xaa Trp Thr Arg Cys Lys
1               5                   10                  15

Lys Lys
```

```
<210> SEQ ID NO 32
<211> LENGTH: 17
<212> TYPE: PRT
<213> ORGANISM: Artificial Sequence
<220> FEATURE:
<223> OTHER INFORMATION: Synthetic peptide derived from SEQ ID NO 11
<220> FEATURE:
<221> NAME/KEY: Xaa
<222> LOCATION: (1)..(17)
<223> OTHER INFORMATION: Xaa is citrulline

<400> SEQUENCE: 32

Cys Lys Asp Asn Ser Asp Xaa Ser Thr Tyr Xaa Thr Arg Cys Lys Lys
1               5                  10                  15

Lys

<210> SEQ ID NO 33
<211> LENGTH: 18
<212> TYPE: PRT
<213> ORGANISM: Artificial Sequence
<220> FEATURE:
<223> OTHER INFORMATION: Synthetic peptide derived from SEQ ID NO 11
<220> FEATURE:
<221> NAME/KEY: Xaa
<222> LOCATION: (1)..(18)
<223> OTHER INFORMATION: Xaa is citrulline

<400> SEQUENCE: 33

Lys Cys Lys Asp Asn Ser Asp Xaa Ser Thr Tyr Xaa Trp Thr Arg Cys
1               5                  10                  15

Lys Lys
```

SYNTHETIC PEPTIDES IMMUNO-REACTIVE WITH RHEUMATOID ARTHRITIS AUTO-ANTIBODIES

SUMMARY OF THE INVENTION

Embodiments of the present invention relate to synthetic peptides that are preferentially recognized by auto-antibodies, specifically by autoimmune antibodies, to be detected in patients afflicted with or at risk for rheumatoid arthritis, enabling enhanced sensitivity and specificity in detection of these auto-antibodies in pre-symptomatic patients as well as patients showing symptoms of rheumatoid arthritis.

Peptides of the present invention have unique sequences, not found in nature, comprising a series of citrulline residues at selected locations along the peptides and also have optimal number of residues in between the citrulline residues. Assembly and sequence of selected amino acid residues confers optimal charge and hydrophobicity to enhance reactivity with autoimmune antibodies. Furthermore, the respective peptides may be cyclized. Such cyclized synthetic peptides may be further multimerized in series as monomers, dimers, trimers and multimers. Surprisingly, the combination of citrulline residue spacing in designed synthetic antigen mimetic peptide sequences, as well as multimer mixtures according to embodiments of the invention, proved to be very suitable for the enhanced diagnosis of rheumatoid arthritis. These synthetic peptides preferably have the following general formula:

$[X(aa)_n X]_m$, where $X$=citrulline residue, $aa$=amino acid with $n$=0 to 8, $m \geq 1$.

According to one aspect of the present invention, there is provided a synthetic peptide consisting of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:28, SEQ ID NO: 30, SEQ ID NO:31, SEQ ID NO:32, and SEQ ID NO: 33. In further embodiments, the peptides may be cyclized.

According to another aspect of the invention, there is provided a composition for detecting autoimmune antibodies expressed by patients at risk for or afflicted with rheumatoid arthritis, the composition comprising at least one peptide consisting of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO: 30, SEQ ID NO:31, SEQ ID NO:32, SEQ ID NO: 33 and combinations thereof. In further embodiments, the peptides of the composition may be cyclized. In further embodiments, the peptides may be cyclized in series as monomers, dimers, trimers and multimers.

According to another aspect of the invention, there is provided a composition comprising at least two peptides consisting of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO: 30, SEQ ID NO:31, SEQ ID NO:32, and SEQ ID NO: 33, wherein at least two of said at least two peptides are cyclized. In further embodiments, the peptides may be cyclized in series as monomers, dimers, trimers and multimers.

According to another aspect of the invention, there is provided a synthetic peptide selected from the group consisting of: a) a synthetic peptide comprising two or more citrulline residues separated by 0-8 amino acid residues; b) a synthetic peptide comprising amino acid sequences derived from proteins containing two or more citrulline residues separated by 0-8 amino acid residues; and c) a peptide comprising citrulline residues of the general formula:

$[X(aa)_n X]_m$, where $X$=citrulline residue, $aa$=amino acid with $n$=0 to 8, $m \geq 1$.

According to yet another aspect of the invention, there is provided a method for detecting autoimmune antibodies expressed by patients at risk for or afflicted with rheumatoid arthritis comprising the steps of contacting a synthetic peptide of the present invention with a plasma or serum sample from a patient and detecting the presence or absence of antibody-antigen complex, wherein the presence of the antibody-antigen complex indicates the presence of autoimmune antibodies, and wherein the presence of autoimmune antibodies indicates said patient is at risk for or is afflicted with threumatoid arthritis.

According to another aspect of the present invention, there is provided a method for micro-array format diagnosis of rheumatoid arthritis comprising the steps of: preparing a synthetic peptide sequence of the present invention; providing a biological sample for diagnosis of rheumatoid arthritis; bringing said biological sample into contact with said artificial antigen under conditions allowing the formation of an antigen/antibody complex with the auto-antibodies specific for rheumatoid arthritis which may be present in said biological sample; and detecting any antigen/antibody complexes which may be formed.

BRIEF DESCRIPTION OF THE DRAWINGS

FIG. 1 is a depiction of nine exemplary peptide sequences in accordance with embodiments of the present invention illustrating a series of conjugated residues, to show the numbers and specific locations of citrullines in the sequences and exemplary spacing inbetween citrulline residues;

FIG. 5 is a table depicting exemplary peptides of the present invention.

DESCRIPTION OF THE PREFERRED EMBODIMENTS

Figure 2:
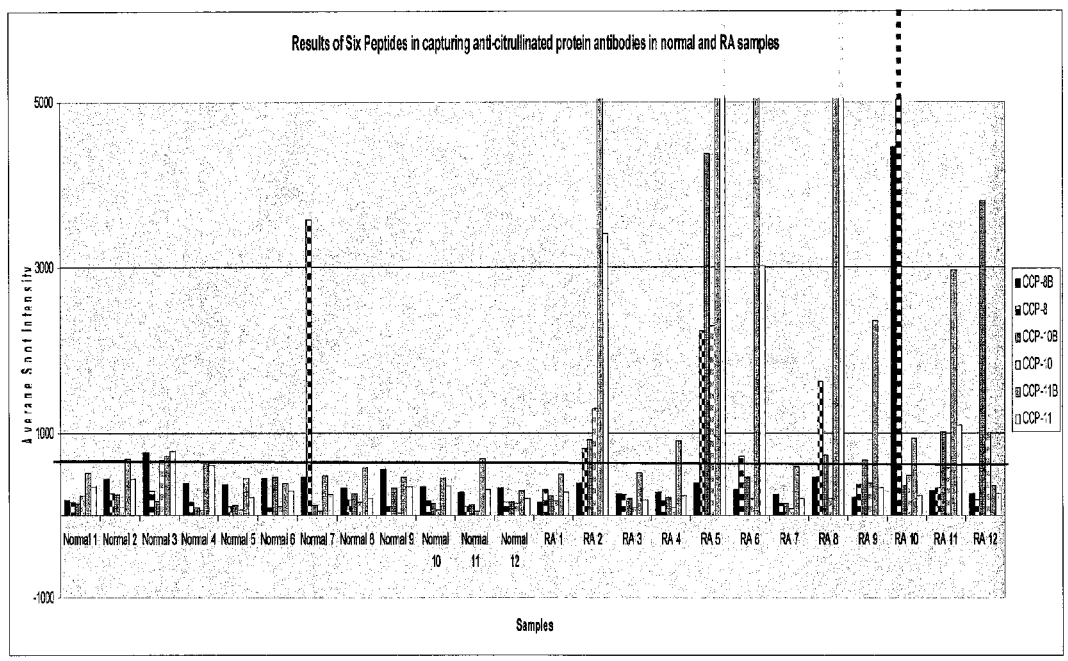
FIG. 2 is a bar graph showing a signal intensity for the presence synthetic peptide auto-antibody complex for six of the exemplary synthetic peptides of the present invention in rheumatoid arthritis and non-rheumatoid arthritis patient serum samples.

Rheumatoid arthritis is a systemic autoimmune disease and is considered the most frequent of the chronic inflammatory rheumatisms. The serum of affected patients contains auto-antibodies, a proportion of which are specific to constitute a marker for this disease, allowing its diagnosis even at early stages. Wide ranging methods have been published, in a search to find and identify antigens recognized by these antibodies and purified antigen preparations which can be used in conventional immunological diagnostic techniques.

Analyte-antibody protein interactions play a key role in the control of molecular events involved in signal transduction. Comparatively large surface profiles at these protein-protein interfaces make the design and accessibility of small molecule interactive sites spatially hindered. The energetic residues actively modulating protein-protein interfaces use relatively small regions of the protein surface. Correctly selected Protein Epitope Mimetic (PEM) molecules which mimic surface epitopes, provide a means of mimicking the biological activity of an entire protein in relatively small synthetic, molecular, spatially accommodating, three dimensional macromolecular recognition sites. Peptide-mimetic design starts with three dimensional structures of peptides and the conjugated mimetic complexes they form, applying insights into the type and location of residue matrix structures. This represents an area of organic chemistry where matrix conformation and mechanisms of binding confirm design and synthesis of biologically active organic molecular matrices.

There is therefore a need for synthetic peptides that bind with high sensitivity to auto-antibodies, specifically by autoimmune antibodies to be detected in patients afflicted with rheumatoid arthritis, enabling enhanced sensitivity and specificity in detection of these auto-antibodies in pre-symptomatic patients as well as patients showing symptoms of rheumatoid arthritis. There is a need for such a peptide that is recognized by rheumatoid arthritis-specific autoimmune antibodies. There is a further need for the detection of anti-citrullinated rheumatoid arthritis auto-antibodies by novel, multiple designer peptides to provide enhanced sensitivity and specificity for more accurate quantitative relative measurement of auto-antibody concentration.

Embodiments of the present invention involve the synthesis of synthetic peptide mimetic epitopes. Select, potent antigenic determinants may be assembled into peptide matrices containing these determinants; the sensitivity and specificity of contiguous amino acid sequences in a linear array (continuous epitope) and amino acids in close proximity in the folded protein, but distant when unfolded (discontinuous epitope) form peptide matrices designed to mimic immunodominant epitopes of antigen. In certain embodiments, the epitope can be a localized region on the surface of an antigen that is capable of eliciting an immune response.

The synthetic peptides of the present invention have unique sequences containing series citrulline residues at selected locations along the peptides and may also have optimal number of residues inbetween the citrulline residues. Surprisingly, assembly and sequence of selected amino acid residues confers optimal charge and hydrophobicity to enhance reactivity with autoimmune antibodies. In further embodiments, the respective peptides may be cyclized in series as monomers, dimers, trimers and multimers. In certain embodiments, a mutiplex of designed peptide sequences may be suitable for the diagnosis of rheumatoid arthritis.

Methods of cyclizing peptides are well known in the art. For example such methods are described in Cline D. J., Thorpe C., Schneider J. P. General method for facile intramolecular disulfide formation in synthetic peptides, Analytical Biochemistry 335:168-170 (2004) which is hereby incorporated by reference.

Methods of creating dimers and multimers are also well known in the art. For example such methods are described in Marini M. A., Moore G. L., Christensen S. M., Fishman R. M., Jessee R. G., Medina F., Snell S. M., Zegna, A. I, Reexamination of the polymerization of pyridoxylated hemoglobin with glutaraldehyde., Biopolymers 29:871-882 (1990) which is hereby incorporated by reference.

In embodiments of the present invention, the synthetic peptides have the following formula:

$[X(aa)_nX]_m$, where $X$=citrulline residue, $aa$=amino acid with $n$=0 to 8, $m \geq 1$.

Exemplary peptides of the foregoing formula include, but are not limited to, SEQ ID NO:1 to SEQ ID NO:33.

FIG. 1 shows nine exemplary peptides in accordance with embodiments of the present invention. Each peptide is numbered and has citrulline residues indicated by the letter X. The series of conjugated residues show the X repeats at specified locations in the sequences and the distance that the X's are separated from each other. Peptides of SEQ ID NO:30, SEQ ID NO:19, SEQ ID NO:22, SEQ ID NO:28 and SEQ ID NO:8 respectively with respective X-X spacing of 3, 0, 1-1, and 2 amino acid intervals and when used in the multiple peptide mix in a format ratio of about 1:1, resulted in high autoantibody signal.

In further embodiments, the peptides may further comprise optional residues, for example those with inherent disulfide bonds that allow for these peptides to be cyclized, or linked in an intermolecular manner to maximize the structural and chemical stability. Cyclizing has the added advantage in providing a spatial perspective to the peptides.

Another embodiment of the present invention is a composition to provide optimal antigen binding of rheumatoid arthritis auto-antibodies comprising the peptides of SEQ ID NO:30, SEQ ID NO:19, SEQ ID NO:22 and SEQ ID NO:28 and SEQ ID NO:23 in an about 1:1 mixture.

The design of these synthetic antigen mimetic peptides ensures the placing of flexible residues, such as glycine, serine or threonine, in the vicinity of citrulline residues and also to contain residues that are smaller to allow flexibility of a peptide. Such residues include glycine and serine, which are commonly used as linkers between protein domains, including as single chain antibodies. These peptides should include soluble residues, such as arginine, glutamine and leucine, to maintain a balanced charge and to maintain a relatively non-neutral pH. Surprisingly, when the multiple synthetic antigen mimetic antigen embodiment of the present invention is used in a micro-array assay format, cyclization of the peptides also improves stability of the capture antigen and its ability to be immobilized on the assay substrate.

Further embodiments of the present invention are compositions of the synthetic peptides as monomers, dimers, trimers and multimers. Such compositions may provide a beneficial effect in increasing detection efficiency. For example, a synthetic peptide may be in the composition as a monomer as follows where the amino acids are shown a single letter codes: CKDNSDXSTYXWTRCK. An example of a dimer is as follows: CKDNSDXSTYXWTRCK+CKDNSDXSTYXWTRCK. An example of a trimer is as follows:

CKDNSDXSTYXWTRCK+CKDNSDXSTYXWTRCK+CKDNSDXSTYXWTRCK. An example of a multimer is as follows: [CKDNSDXSTYXWTRCK]+Xn.

In a further embodiment, the peptides of the present invention may be included in a composition that is contacted with a fluid sample of a patient to be tested for existence or predisposition for rheumatoid arthritis. The composition can include one or more of the synthetic peptides of SEQ ID NO:1 to SEQ ID NO:33. For example, the composition includes the peptides consisting of the amino acid sequences SEQ ID NO:19, SEQ ID NO:22, SEQ ID NO:23, SEQ ID NO:28, and SEQ ID NO:30 in a weight ratio of about 1:1:3:3:3.

In general, the synthetic peptide sequences of the present invention may be mixed in a composition in weight ratios of about 1 to 3; preferably in a weight ratio of about 1 to 1.

In certain embodiments, the peptide sequences may be mixed in compositions at a concentration range of about 10 milligram per milliliter to about 1 microgram per milliliter; preferably at a concentration of about 3 milligrams per milliliter.

Once the plasma or serum sample from a patient is contacted with the mixture comprising the synthetic peptides of the present invention, the resulting antibody/peptide complex can be detected by methods known in the art. For example, the complex may be fluorescently labeled and the intensity of fluorescence may be measured. The level of fluorescence will be directly proportional to the level of binding of the synthetic peptides to the autoimmune antibodies expressed as a result of rheumatoid arthritis.

Embodiments of the present invention may be further explained and exemplified by means of the following example.

Material and Methods.

Peptides were cyclized by oxidizing the cysteine residues of the peptides to form intramolecular disulphide bond. Following cyclization, the peptides were conjugated through glutaraldehyde facilitated multimerization for 12-20 hours. The excess glutaraldehyde was removed by reaction with sodium borohydride. The conjugated peptides were then purified using a membrane based spin filtration column. The resulting peptides were quantified by spectrophotometry.

The conjugated peptides were either individually made or mixed together into microarray printing buffers. The resulting solutions were printed using a non-contact microarray printer. The resulting microarrays were conditioned to optimize the printed peptides and blocked. The printed microarray was then tested for the reactivity of the synthetic antigen mimetic peptides, specifically, their ability to capture anti-citrullinated protein antibodies using a microarray assay.

In this assay, the serum samples containing zero, low, medium and high levels of anti-citrullinated protein antibodies were loaded onto the microarray into 96 reaction wells per microtiter formatted microarray plate. After 30 min incubation, the excess amount of the serum sample was removed. And the microarray was washed in a plate washer. Subsequently, a mixture of labeled anti-human IgA, IgG and IgM antibodies were added and incubation was timed to continue for 30 min. Following another plate washing step, the microarray wells were then dried and fluorescence read in a microarray reader.

In some assays, in addition to the citrullinated peptides, rheumatoid factor reagents were also printed into each well, in order to simultaneously detect anti-rheumatoid factor IgA, rheumatoid factor IgG, rheumatoid factor IgM and anti-citrullinated protein antibodies. For all assays, proprietary assay data analysis software was used to integrate the spot intensity, and optionally, to standardize the signals into concentrations value.

Results

Individual Peptides Tested

Six synthetic peptides, peptides 8B, 8, 10B, 10, 11B and 11 [SEQ ID NO:23, SEQ ID NO:24, SEQ ID NO:26, SEQ ID NO:27, SEQ ID NO:29 and SEQ ID NO: 30] were prepared according to the above method and the resulting microarray plates were tested using 24 samples. Responses for each samples for each peptide was analyzed and plotted. Results were fluorescence intensity values for each samples plotted against the identities of the samples. The thick line indicates a cut-off threshold, as shown in FIG. 2.

Testing to Establish the Quantitative Response of the Multimer Mix

Figure 3:
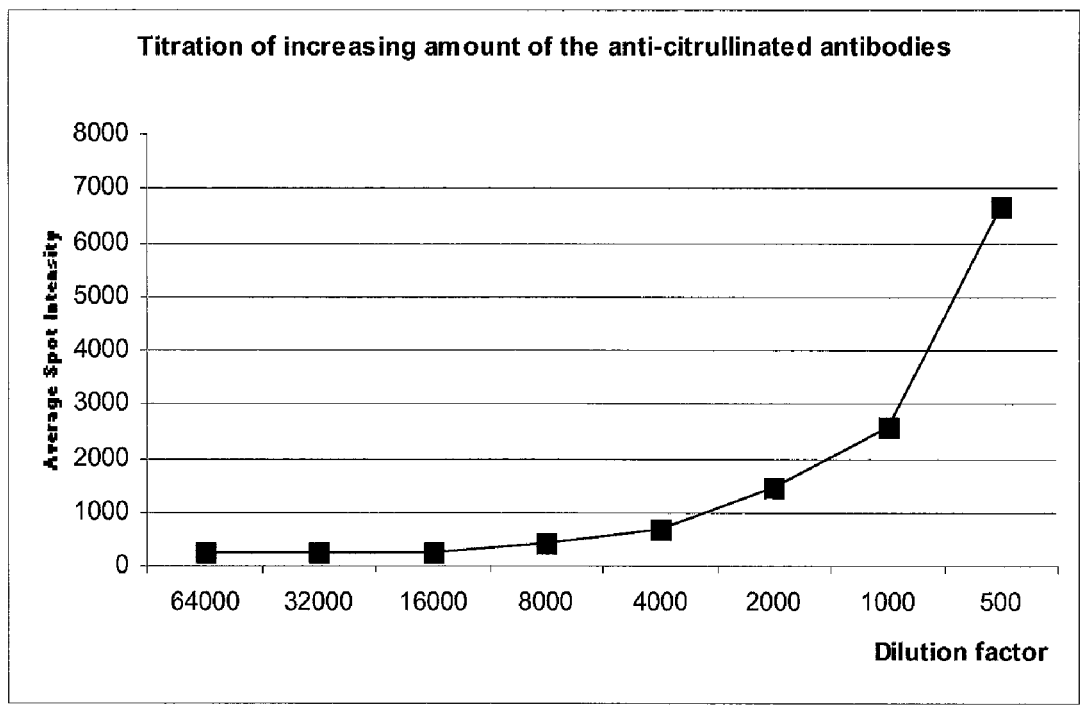
FIG. 3 is graph showing signal intensity directly proportional to the presence of synthetic peptide/antibody complex as detected in a dilution series of multiplex antigen.

A mixed pool of two samples was diluted with the indicated dilution factor and tested using the assay described above. Results were fluorescence intensity values for each samples plotted against the identities of the samples. A progressive increase in the response from the most dilute sample to least diluted sample was observed as shown in FIG. 3.

Figure 4:
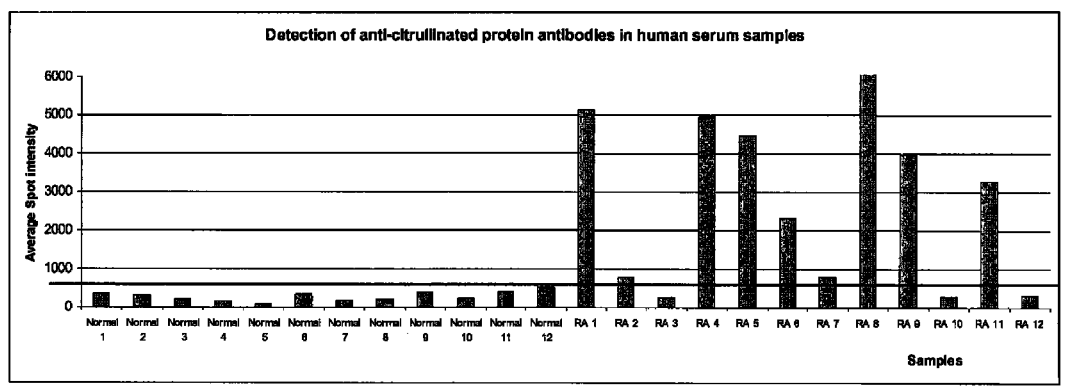
FIG. 4 is a bar graph showing a comparison of signal intensity showing the presence of synthetic peptide/antibody complex in rheumatoid arthritis and non-rheumatoid arthritis patient serum samples.

Testing Using a Panel of Normal and Patient Samples Using the CCP Mix 12 samples obtained from healthy donors and tested to be normal by a commercial ELISA kit and 12 samples obtained from known rheumatoid arthritis patients and confirmed by testing using several ELISA kits were tested. Results were fluorescence intensity values for each sample plotted against the identities of the samples. The thick line indicated a cut-off threshold that was used to distinguish the samples into the final testing results. The 12 normal samples were all found to be normal and 9 of the 12 samples were found to be positive for the anti-citrullinated protein antibodies, as shown in FIG. 4.

While the present invention has been described with reference to the details of the embodiments of the invention as illustrated in the figures, these details are not intended to limit the scope of the invention as claimed in the appended claims.

What is claimed is:

1. A synthetic peptide consisting of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:19, SEQ ID NO:22, SEQ ID NO:23, SEQ ID NO:28, and SEQ ID NO:30.

2. The synthetic peptide of claim 1, wherein said peptide is cyclized.

3. A composition comprising a carrier and a peptide consisting of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:19, SEQ ID NO:22, SEQ ID NO:23, SEQ ID NO:28, SEQ ID NO:30, and combinations thereof.

4. The composition of claim 3, wherein the composition comprises the peptides consisting of the amino acid sequences SEQ ID NO:19, SEQ ID NO:22, SEQ ID NO:23, SEQ ID NO:28, and SEQ ID NO: 30.

5. The composition of claim 4, wherein the peptides have a weight ratio of about 1:1:3:3:3.

6. The composition of claim 3, wherein the composition comprises a dimer of amino acid sequences.

7. The composition of claim 3, wherein the composition comprises a trimer of amino acid sequences.

8. The composition of claim 3, wherein the composition comprises a multimer of amino acid sequences.

9. The composition of claim 3, wherein said peptide is cyclized.

10. A composition comprising at least two peptides consisting of an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:19, SEQ ID NO:22, SEQ ID NO:23, SEQ ID NO:28, SEQ ID NO:30 and wherein said at least two peptides are cyclized.

11. A method for detecting autoimmune antibodies expressed by a patient at risk for or afflicted with rheumatoid arthritis comprising the steps of contacting a synthetic peptide of claim 1 with a sample from a patient and detecting the presence of an antibody-antigen complex, wherein the presence of said antibody-antigen complex indicates the presence of autoimmune antibodies.

12. The method of claim 11, wherein the presence of said antibody-antigen complex indicates said patient is at risk for or is afflicted with rheumatoid arthritis.

13. The method of claim 11, wherein said sample from a patient is selected from plasma and serum.

14. The method of claim 11, further comprising the step of quantifying an immuno-reactivity of the synthetic peptide with the autoimmune antibodies.

15. The method of claim 14, wherein at least three immunoglobulins are quantified.

16. The method of claim 15, wherein said at least three immunoglobulins are immuno-globulin IgG, immuno-globulin IgA and immuno-globulin IgM.

17. The method of claim 15, wherein quantification comprises the use of enzyme-linked immuno-sorbent assay immuno-chemistry (ELISA).

18. A method for detecting autoimmune antibodies expressed by a patient at risk for or afflicted with rheumatoid arthritis comprising the steps of mixing a composition of claim 3 with a sample from a patient and detecting the presence of an antibody-antigen complex, wherein the presence of said antibody-antigen complex indicates the presence of autoimmune antibodies.

19. A method according to claim 18 wherein the composition comprises the peptides consisting of the amino acid sequences SEQ ID NO:19, SEQ ID NO:22, SEQ ID NO:23, SEQ ID NO:28, and SEQ ID NO:30.

20. A method of diagnosing rheumatoid arthritis in a patient, wherein the improvement comprises: utilizing the synthetic peptide of claim 1 for the diagnosis of rheumatoid arthritis in the patient.

* * * * *